United States Patent [19]

Nelson et al.

[11] Patent Number: 4,804,699

[45] Date of Patent: * Feb. 14, 1989

[54] MONOMERIC AND OLIGOMERIC GLUTARATE-BASED LIGHT STABILIZERS FOR PLASTICS

[75] Inventors: Richard V. Nelson, Wilmington, Del.; John F. Stephen, West Chester, Pa.

[73] Assignee: ICI Americas Inc., Wilmington, Del.

[*] Notice: The portion of the term of this patent subsequent to Aug. 25, 2004 has been disclaimed.

[21] Appl. No.: 50,077

[22] Filed: May 15, 1987

[51] Int. Cl.$^4$ ................ C07P 401/12; C07D 401/14; C08K 5/34

[52] U.S. Cl. ..................................... 524/98; 524/102; 524/103; 540/523; 546/19; 546/187

[58] Field of Search .................. 524/102, 103, 98; 546/19, 187; 540/523

[56] References Cited

U.S. PATENT DOCUMENTS

| | | | |
|---|---|---|---|
| 4,689,360 | 8/1987 | Nelson et al. | 524/98 |
| 4,701,485 | 10/1987 | Nelson et al. | 524/98 |
| 4,710,527 | 12/1987 | Nelson et al. | 524/98 |

*Primary Examiner*—John Kight
*Assistant Examiner*—Kriellion Morgan

[57] ABSTRACT

Monomeric and oligomeric derivatives of the dialkyl esters of polyalkyl 1,5-dioxa-9-azaspiro-[5.5]undecane-3,3-diacetic acid are useful light stabilizers for synthetic polymer resins such as polyolefins, and in particular, polypropylene.

12 Claims, No Drawings

MONOMERIC AND OLIGOMERIC GLUTARATE-BASED LIGHT STABILIZERS FOR PLASTICS

The invention pertains to polymeric compositions which are resistant to degradation when exposed to actinic radiation. In particular, it is directed to resins such as polypropylene stabilized with effective amounts of cyclic acetals of polyalkyl 4-oxopiperidine. The invention is further directed to a novel group of glutarate based derivatives which are useful as additives for synthetic polymers by acting to retard photo-degradation and to a process for their manufacture.

Many synthetic organic polymers deteriorate rapidly when exposed to sunlight. To circumvent this rapid degradation many additives have been developed to stabilize these resins against the harmful radiation. These additives include hydroxybenzophenones, hydroxybenzotriazoles, organonickel complexes, and a number of compounds which incorporate a hindered amine, such as 2,2,6,6-tetraalkylpiperidine, that is substituted in the 4-position. However, because none of these compounds sufficiently satisfy the stabilization requirements of polymers in their wide variety of forms and applications, there remains a need for new substances which will be more fully satisfactory.

Stable synthetic polymer compositions of the invention are made by their incorporation with of an effective amount of novel acetals derived from a hindered piperidine compound. These compounds may be selected from structures defined by formula I as shown in the Table of Structures wherein:

$R^1$ is selected from hydrogen and an alkyl group of 1 to 5 carbon atoms such as methyl, ehhyl, n-propyl, n-butyl, n-pentyl but is preferably hydrogen and methyl, and most preferably, hydrogen;

$R^2$ is selected from hydrogen, oxyl, hydroxyl, a straight or branched chain methylene-linked alkyl group from 1 to 18 carbon atoms, such as methyl, ethyl, octyl, octadecyl or 2-ethylhexyl, an alkanoyl group having 2 to 18 carbon atoms, such as acetyl, propanoyl, butanoyl, isopentanoyl, or stearoyl, an alkenyl group of 3 to 4 carbon atoms, an alkenoyl group having 3 to 6 carbon atoms, such as acryloyl, methacryloyl, crotonyl, 2,3-dimethylcrotonyl, an alkynyl group having 3 to 6 carbon atoms such as propynyl or 2-butynyl, a cyanomethyl group, 2,3-epoxypropyl group, an aralkyl group of 7 to 15 carbon atoms such as 3,5-di-tert-butyl-4-hydroxybenzyl, 2-tert-butyl-4-hydroxybenzyl, or 3-tert-butyl-4-hydroxy-5-methylbenzyl, a group —CH$_2$CH(OR$^5$)—R$^6$, and a group of the formula

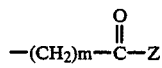

wherein m is either 0 or 1 and Z is a group selected from —OR$^7$; —N(R$^8$)(R$^9$) and

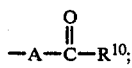

when m is 0, Z can be a group —C(O)—OR$^{11}$ $R^3$ and $R^4$, same or different, are selected from an alkyl group of 1 to 18 carbon atoms such as $R^2$, and hydrogen and a group of the formula II, $R^5$ is selected from hydrogen, an aliphatic group of 1 to 18 carbon atoms such as those of $R^2$, an araliphatic group such as benzyl and phenethyl, and an aliphatic acyl group of 2 to 18 carbon atoms such as those of $R^2$;

$R^6$ is selected from hydrogen, an alkyl group of 1 to 16 carbon atoms such as thos of $R^2$, and phenyl;

$R^7$ is selected from an alkyl group of 1 to 18 carbon atoms, a cycloalkyl group of 5 to 12 carbon atoms such as cyclopentyl, cyclohexyl, cyclooctyl, and cyclododecyl, allyl, benzyl, phenyl, and a group of formula II wherein $R^1$ and $R^2$ are as described above;

$R^8$ and $R^9$, same of different, are selected from hydrogen, an alkyl group having 1 to 8 carbon atoms such as methyl, ethyl, hexyl, a cycloalkyl group having 5 to 12 carbon atoms such as 4-methylphenyl, 2-methylphenyl, 4-butylphenyl, and aralkyl groups having 7 to 15 carbon atoms such as benzyl, o, m, and p-alkyl-substituted benzyl, and phenethyl, and, $R^8$ and $R^9$ together with the nitrogen atom to which they are attached can form a 5 to 7-membered ring such as pyrrolidine, piperidine and homopiperidine;

A is selected form a straight or branched chain alkylene group of 1 to 12 carbon atoms, phenylene and a group —NH—R$^{12}$—N— where R$^{12}$ is selected from an alkylene group of 2 to 18 carbon atoms, either straight chained or branched, a cycloalkylene group having 5 to 18 carbon atoms, an aralkylene group having 7 to 18 carbon atoms, and alkylene group having 6 to 18 carbon atoms, and R$^{10}$ is a group of the formula III, $R^{11}$ is selected from an unsubstituted alkyl group of 1 to 18 carbon atoms, phenyl and benzyl and s preferably an alkyl group having 1 or 2 carbon atoms:

p and q, independently, can be either 0 or 1; wherein n has a value of 1 to 15.

When n is 1, p and q can be 1 or 0: when n is greater than 1, p is 1, while q may be 1 or 0.

X is either —O— or —NR$^{13}$— where R$^{13}$ is selected from hydrogen or an alkyl group of 1 to 8 carbon atoms such as methyl, ethyl, butyl or octyl;

Y is a divalent alkylene group having 2-20 carbon atoms, either straight-chained or branched, wherein the alkylene may be interrupted by —O—, —S— or —NR$^1$—, also Y may be selected from a cycloalkylene group of 6-12 carbon atoms such as cyclohexanyl and cyclooctanyl and dialkanylcycloalkane such as dimethanocyclohexane, diethanocyclohexane, dicyclohexanylmethane, dicyclohexanylethane, dimethanocyclohexylmethane, diethanocyclohexylmethane, diethanocyclohexylethane, 2,2-dicyclohexanylpropane, a phenylene group and an aralkylene group having 8 to 19 carbon atoms such as dimethanobenzene and 4,4'-isopropylidenediphenyl and ethanooxy substituted aralkylene. The oligomers represented by formula I may range in molecular weight from about 650 to 10,000.

The compounds of formula I may be prepared in a multistep process. The first step in the process (n is 1, p and q are 0, X is —O—) is the preparation of the acetal derived from the diol (HOCH$_2$)$_2$C(CH$_2$Q)$_2$ with a 4-oxopolyalkylpiperidine of the formula III using a suitable acid catalyst and a suitable solvent as generally known in the art for the preparation of acetals. Examples of suitable acid catalysts are numerous, however, without introducing any limitations are mentioned p-toluenesulfonic acid and methanesulfonic acid. Examples of suitable solvents are cyclohexane and benzene. The compound of formula V can be either the free amine or the acid addition salt. Examples of such acid addition salts include those derived from hydrogen chloride, hydrogen bromide, sulfuric acid, phosphoric acid, and the like, as well as those of strong organic acids like paratoluenesulfonic acid and methanesulfonic acid. The group Q may be any halogen which can serve as a leaving group such as chlorine, bromine and iodine but it is preferred that Q be chlorine or bromine because the corresponding diols are available commercially. Alternatively the preferred diols can be prepared by the chlorination or bromination of pentaerythritol as described in U.S. Pat. Nos. 3,607,953 and 3,932,541.

The reaction of 2,2,6,6-tetraalkyl-4-piperidones with dihydroxy substances to form the corresponding acetal derivatives is well-known and techniques similar to those described in U.S. Pat. Nos. 3,790,525; 3,899,464; 4,007,158; 4,105,626; and EP 22,997 may be employed. Of particular interest as a starting component is 2,2,6,6-tetramethyl-4-piperidone. Preparative procedures for this ketone may be found throughout the literature and in U.S. Pat. No. 4,105,626, Column 9. Specifically the compound is prepared by the reaction of ammonia with acetone. The dibromoacetal derived from 2,2,6,-tetramethyl-4-piperidone and dibromoneopentyl glycol has been reported previously by Czech workers in CS 225,050.

The preparation of other polyalkylpiperidin-4-ones of formula IV can be prepared by reaction of ammonia with an aliphatic ketone such as methyl ethyl ketone. This procedure has been described by W. Traube in Chem, Ber. 41,777 (1908).

Compounds of the formula III which carry other alkyl substituents in the 2-position and the 6-position can be prepared in a two step process following the procedures outlined in Helv. Chim. Acta 30,1114(1947) and Monatsh.Chem. 88,464(1957), followed by hydrolysis of the resulting pyrimidine.

The acetalization reaction is generally carried out in a refluxing solution of a water-immiscible solvent at a temperature of about 80° C. in the presence of an acid catalyst. Solvents which work well are cyclohexane and benzene as well as others that may be useful. Acid catalysts which are commonly utilized are organic acids such as methanesulfonic acid, paratoluenesulfonic acid and others which are considered useful.

The acetal resulting from reaction of the dihaloneopentyl glycol and the appropriate piperidin-4-one is generally isolated by solvent extraction and after concentration can be purified by either distillation or crystallization.

The resultant dihaloacetals for formula V can be transformed into the compounds of the invention via the sequence: cyanation, hydrolysis, esterification, and then either simple transesterification or oligomerization.

In general the cyanation is performed in a dipolar aprotic solvent such as dimethyl sulfoxide, dimethyl formamide, N-methylpyrrolidone, and the like using a cyanide salt such as sodium cyanide or potassium cyanide. The reaction can be carried out at a temperature ranging from 20° C. to 160° C. but it is preferred that the reaction be run at about 100°-130° C. The resulting dinitrile can be isolated by solvent extraction and can be purified by crystallization.

The dinitriles are then transformed into the corresponding diesters by hydrolyzing the nitrile to the carboxylate salt using aqueous alkaline conditions such as potassium hydroxide and sodium hydroxide. A cosolvent can be used to help solubility of the substrate in the aqueous mixture such as an alcohol like ethanol or a dipolar aprotic solvent like dimethyl sulfoxide.

The resulting salt can be esterified using an alkyl halide or dialkyl sulfate such as methyl chloride, methyl iodide, dimethyl sulfate, diethyl sulfate, etc.

The dialkyl spiroacetal can be used as a starting material for the next step in the process. Higher molecular weight monomeric esters and amides can be prepared by reaction of the dialkyl spiroacetal, neat or in solution, with higher molecular weight monofunctional alcohols, amines or mixtures thereof using a basic catalyst like lithium amides or titanium tetraisopropoxide. Examples of suitable solvents include ligroine and toluene. Oligomers and polymers wherein n is greater than 1 up to a value of about 15 and preferably having a value of 2 to 10 are formed under similar conditions employing difunctional alcohols, amines or mixtures thereof.

The products may be separated from solvent solution and are generally purified by the trituration or crystallization or any other suitable procedure.

The 4-hydroxypolyalkylpiperidines and the 4-aminopolyalkylpiperidines used to convert the acetals into the compounds of the invention are know from German Patent No. 2,352,658 and U.S. Pat. No. 3,684,765. In general, the 4-hydroxy compounds are prepared from the corresponding 4-oxopiperidines by reduction via catalytic hydrogenation over Raney Nickel and the 4-amino compounds are synthesized via a reductive amination using ammonia or the particular primary amine of interest.

The introduction of an alkyl, alkenyl alkynyl, aralkyl and 2,3-epoxypropyl group can be achieved by reaction of the initially prepared acetal containing the free N-H of the polysubstituted piperidine with suitable halides like methyl iodide, ethyl bromide, propyl bromide, dodecyl chloride, and octadecyl chloride; allyl bromide, methallyl chloride, butenyl chloride, propargyl bromide, benzyl chloride, phenethyl bromide, and epichlorohydrin. The generated hydrogen halide can be scavenged by the addition of an inorganic base such as carbonate or hydroxide or by the addition of an organic amine such as triethylamine to the reaction mixture.

The introduction of an alkanoyl or an alkenoyl group can be performed by acylation of the parent N-H compound using the suitable acid halide or, when convenient, the acid anhydride. If the acid halide is used the generated hydrogen halide can be scavenged in the same manner as stated previously. Examples of such groups are acetyl chloride, propionyl chloride, hexanoyl chloride, dodecanoyl chloride, octadecanoyl chloride, acetic anhydride, and propionic anhydride. Similarly the oxalyl chloride monoester can be introduced using reagents such oxalyl chloride monomethyl ester and oxalyl chloride monoethyl ester.

For the compounds when $R^2$ is the group —$CH_2CH(OR^5)$—$R^6$ the substituent can be introduced by reaction of the parent N-H compound with the corresponding alkylene oxide such as ethylene oxide, propylene oxide and styrene oxide. The resulting hydroxy compound can be acylated in the manner commonly known in the art using the suitable acid halide and can be alkylated by generatng the alkoxide using a base like sodium hydride and treating it with the desired alkyl or aralkyl halide.

When $R^2$ is the group $-(CH_2)_m COZ$ and m is 0 the appropriate group can be attached by reacting the parent N-H compound with a chloroformate such as methyl chloroformate, ethyl chloroformate, allyl chloroformate, hexyl chloroformate, decyl chloroformate, octadecyl chloroformate, and phenyl chloroformate.

For preparation of the corresponding ureas the parent N-H compound can be treated with the suitable carbamyl halide such as methyl carbamyl chloride, ethyl carbamyl chloride, butyl carbamyl chloride, phenyl carbamyl chloride, dimethyl carbamyl chloride, diethylcarbamyl chloride, dihexylcarbamyl chloride, pyrrolidinyl carbamyl chloride, piperidine carbamyl chloride, and homopiperidine carbamyl chloride. Alternatively, the ureas can be prepared by treating the parent N-H compound with the suitable isocyanate.

Compounds of formula I wherein $R^2$ is the oxyl radical are obtainable from the corresponding N-H compounds by oxidation with a peroxide such as hydrogen peroxide in the presence of a catalyst like sodium tungstate or with percarboxylic acids like metha-chloroperoxybenzoic acid.

When $R^2$ is the group $—(CH_2)_m—COZ$ and m is 1 the appropriate group can be attached by reacting the parent N-H compound with an ester of chloroacetic acid such as methyl chloroacetate, ethyl chloroacetate, cyclohexylchloroacetate, ethyl chloroacetate, cyclohexylchloroacetate, benzyl chloroacetate, allyl chloroacetate and phenyl chloroacetate.

The compounds of this invention are effective light stabilizers for synthetic organic polymers.

The following examples are offered to demonstrate but not limit the scope of the invention.

EXAMPLE 1

8,8,10,10,Tetramethyl-1,5-dioxa-9-azaspiro-[5.5]undecane-3,3-diacetic acid, diester with 2,2,6,6-tetramethylpiperidin-4-ol

Preparation A 8,8,10,10-Tetramethyl-1,5-dioxa-9-azaspiro-[5.5]-undecane-3,3-bis(bromomethyl)

A mixture of 2,2,6,6-tetremethylpiperidin-4-one monohydrate (4.33 g, 25 mmol) and dibromoneopentyl glycol (6.56 g, 25 mmol) in 100 ml of cyclohexane was heated to reflux. The paratoluenesulfonic acid catalyst (5.23 g, 27.5 mmol) was added and the produced water was removed via a Dean-Stark trap. After 6 hr the mixture was removed from the heat, cooled to ambient temperature and partitioned with water after destroying the catalyst with aqueous sodium hydroxide. The organic solution was dried ($Na_2SO_4$) and concentrated to yield the product as an off-white solid (9.00 g, 90% recovery). This material was characterized by NMR and mass spectroscopies and used as obtained for the subsequent reaction.

Preparation B 8,8,10,10-Tetramethyl-1,5-dioxa-9-azaspiro-[5.5]undecane-3,3-bis(cyanomethyl)

To a mixture of ground potassium cyanide (3.57 g, 68.6 mmol) in 65 ml of dimethylsulfoxide was added the compound of Preparation A (5.48 g, 17.1 mmol). The mixture was heated to 120°–130° C. for 4 hr after which time it was cooled to room temperature, poured into about 200 ml of water and extracted with ethyl acetate (3×80 ml). The organic solution was back-washed with water, dried ($Na_2SO_4$) and concentrated to yield the product as a viscous orange liquid which solidified upon standing. This material was further purified by bulb-to-bulb distillation (180° C. @0.1 min) to yield 3.17 g (80% yield) of the desired product. Characterization was effected by NMR and mass spectroscopy.

Preparation C 8,8,10,10-Tetramethyl-1,5-dioxa-9-azaspiro[5.5]undecane-3,3-diacetic acid, dimethyl ester A mixture of the dinitrile of Preparation B (2.91 parts) in aqueous potassium hydroxide (1.12 parts) and ethyl alcohol was heated to reflux. Upon completion of the hydrolysis the solvent was removed and replaced with dimethyl sulfoxide. This solution was treated with methyl chloride at about 80°–90° C. Upon completion of the reaction the prodcct was isolated by partitioning between ethyl acetate and water. The organic solution was dried ($Na_2SO_4$) and concentrated to yield the product as characterized by NMR and mass spectroscopy.

To the product of Preparation C (3.57 parts) and 2,2,6,6-tetramethylpiperidin-4-ol (3.30 parts) in 50 ml of ligroine (90°–110° C.) at reflux was added the lithium amide catalyst (0.02 parts). The produced alcohol was removed by intermittent draining of the Dean-Stark trap After reaction completion the mixture was cooled, the catalyst destroyed by the addition of acetic acid (0.06 parts) and the mixture was partitioned between ligrione and water. After drying ($Na_2SO_4$) and concentration the product was obtained. Characterization was carried out using NMR and mass spectroscopy.

EXAMPLE 2

8,8,10,10-Tetramethyl-1,5-dioxa-9-azaspiro-[5.5]undecane-3,3-diacetic acid, oligomeric with 2,2-dimethyl-1,3-propandiol To a mixture of the compound of Preparation C (3.57 parts) and 2,2-dimethyl-1,3-propandiol (1.04 parts) which was under a stream of nitrogen at 150° C. was added lithium amide (0.02 parts). The temperature was maintained for 6 hr whereupon the mixture was cooled, dissolved in methylene chloride, the catalyst was destroyed with acetic acid (0.06 parts) and the solution was washed with water. The organic solution was dried ($Na_2SO_4$) and concentrated to yield the product. The material was characterized by NMR spectroscopy and gel permeation chromatography.

EXAMPLE 3

8,8,10,10-Tetramethyl-1,5-dioxa-9-azaspiro-[5.5]undecane-3,3-diacetic acid, oligomeric amide with 1,6-hexanediamine A mixture of the compound of Example 1 (3.57 parts) and 1,6-hexanediamine (1.18 parts) was heated at 150° C. in the presence of lithium amide and maintained for 18 hours. The crude reaction mixture was cooled, dissolved in methylene chloride and washed with water. The organic solution was dried (sodium sulfate) and concentrated. The product was characterized by NMR spectroscopy.

The spiroacetal derivatives of the invention are particularly useful as light stabilizers for synthetic polymers which undergo degradation in the presence of air and actinic radiation. As used herein polymers are intended to embrace polyolefins including homopolymers of olefins such as low density and high density polyethylene, polypropylene, polystyrene, polybutadiene, polyisoprene and the like; and copolymers of olefins with other ethylenically unsaturated monomers such as ethylene-propylene copolymer, ethylene-butylene copolymer, ethylene-vinyl acetate copolymer, styrene-butadiene copolymer, acrylonitrilestyrene-butadiene copolymer and the like: polyvinylchlorides and polyvinylidene chlorides including homopolymers of each of vinylchloride and vinylidine chloride, vinylchloride-vinylidene copolymers and copolymers of each vinylchloride and vinylidene chloride with vinyl acetate or other ethylenically unsaturated monomer: polyacetal as such polyoxymethylene and polyoxyethylene; polyesters such as polyethyleneterephthalate; polyamide such as 6-nylon, 6,6-nylon and 6,10-nylon and polyurethanes and polymers derived from α, β-unsaturated acids and derivatives thereof, polyacrylates and polymethacrylates, polyacrylic amides and polyacrylonitrile, as well as copolymers of acrylic acid and one or more of its derivatives with a melamine-formaldehyde resin.

Synthetic polymers have been widely utilized in the art in view of their excellent properties in various forms or shapes, for example, filaments, fibers, yarns, filament sheet, other molded articles and other molded articles made from latex and foam. However, these polymers have some drawbacks such as poor light and heat stabilities among others. Stated illustratively, polyolefins and polyurethane elastomers frequently tend to undergo severe deterioration when exposed to light such as sunlight or ultraviolet light and polyvinyl chloride and polyvinylidine chlorides frequently tend to deterioration when exposed to light such as sunlight or ultraviolet light and polyvinyl chloride and polyvinylidene chlorides frequently tend to deteriorate and become colored by the action of light and heat together with elimination of hydrogen chloride. Polyamides are also frequently subjected to photodegradation. For the purpose of stabilizing these synthetic polymers against such degradation, these have been proposed in the art a number of stabilizers. For example, in the case of polyolefins, benzotriazole and benzophenone compounds: for polyurethanes, phenol compounds and benzophenone compounds: and for polyvinylchlorides and vinylidene chlorides, lead salts such as basic lead silicate and trisilicate, lead maleate and organic tin compounds such as dibutyltinlaurate and dibutyltinmaleate.

The resin should have incorporated within an effective stabilizing amount of a compound described by formula I. The amount will depend upon the nature of the plastic and the amount of radiation to which the plastic will be subject. Generally an amount between about 0.01% and 5.0% by weight of the polymer is effective. Preferably they may be used in concentrations between 0.05 and 1% by weight.

In addition, the light stabilizers of formula I may be used with fillers and additional stabilizers including antioxidants, flame retardant stabilizers, anti-slipping and antistatic agents, supplemental light stabilizers, pigments, dyes, lubricants, etc.

Suitable antioxidants include those of the hindered phenol type such as 2,6-di-t-butyl-p-cresol; 4,4'-bis(2,6-di-t-butylphenol); 4,4'-bis(2,6-diisopropylphenol); 2,4,6-tri-t-butylphenol; 2,2'-thiobis(4-methyl-6-t-butylphenol): octadecyl-2(3',5'-di-t-butyl-4'-hydroxyphenyl)-propionate: pentaerythrityl tetrakis(3,5-di-t-butyl-4-hydroxyphenyl-propionate; 1,3,5-tris(3',5'-di-t-butyl-4-hydroxybenzyl) isocyanurate; 1,3,5-tris((3',5'-di-t-butyl-4'-hydroxyphenyl)propionate) isocyanurate; 1,3,5-tris(3',5'-di-t-butyl-4'-hydroxybenzyl)-2,4,6-dimethylbenzyl)-s-triazine-2,4,6-(1H,3H,5H)-trione and esters of thiodipropionic acid such as dilaurylthiodipropionate and distearylthiodipropionate etc.; hydrocarbyl phosphites such as triphenyl phosphite, trinonyl . phosphite, didodecyl pentaerythrityl diphosphite, diphenyldecyl phosphite, tris-(2,4-di-t-butylphenyl)phosphite, bis(2,4-di-t-butylphenyl)pentaerythritol diphosphite, etc, in combinations thereof.

Suitable supplemental light stabilizers include those of the benzotriazole class, such as 2-(2'-hydroxy-5-t-octylphenyl)benzotriazole; 2,(2'-hydroxy-3',5'-di-t-butyl-phenyl)-5-chlorobenzotriazole: 2-(2'-hydroxy-5'-methylphenyl)benzotriazole; 2-(2'-hydrox-3'-t-butyl-5'-methylphenyl)-5-chlorobenzotriazole: 2-(2'-hydroxy-3',5'-di-t-amylphenyl)benzotriazole: those of the hydroxybenzophenone type such as 2-hydroxy-4-methoxybenzophenone; 2-hydroxy4-octyloxybenzophenone; 2,2'-dihydroxy-4,4'-dimethoxybenzophenone: hindered phenol esters, such as n-hexadecyl-3,5-di-t-butyl-4-hydroxybenzoate: and 2',4'-di-t-butylphenol-3, 5-di-t-butyl-4-hydroxybenzoate; metal complexes such as nickel complexes of 2,2'-thiobis(4-6-octylphenol), nickel butylamine complexes of 2,2'-thiobis(4-t-octylphenol); nickel dibutyl thiocarbamate: nickel salts of 4-hydroxy-3,5-di-t-butylbenzylphosphonic acid monoalkyl esters where alkyl is methyl, ethyl, propyl, butyl etc.: nickel complexes of to 2-hydroxy-4-methylphenyl undecylketoneoxime. Further illustrative examples of suitable antioxidants of supplemental light stabilizers can be found in columns 3 and 4 of U.S. Pat. Nos. 3,488,290 and 3,496,134.

EXAMPLE 4-7

In order to further illustrate the effectiveness of the above-described compounds as light stabilizers the previously described materials of Examples 1-3 were each incorporated into a commercially available polypropylene resin manufactured by Hercules Corporation as PRO-FAX ® 6301 Polypropylene Resin. The light stabilizers were incorporated with the polypropylene by solvent blending (methylene chloride) at concentrations of 0.25% by weight of the total resin composition and as a primary antioxidant stearyl beta-3,5-di-t-butyl-4-hydroxyphenylpropionate was used at a concentration of 0.2%. The resin was then extruded at 200° C. and compression molded at 6,000 psi at 188° C. to produce films having thicknesses of 5 mils. A control film was produced by an identical procedure with the light stabilizer omitted. Each film was exposed to Xenon Arc in an Atlas Weather-ometer until the infrared carbonyl absorption increased by 0.5, which is considred to be the failure point. Time-to-failure is expected to be 8-10 times that of the control having no stabilizer.

TABLE OF STRUCTURES

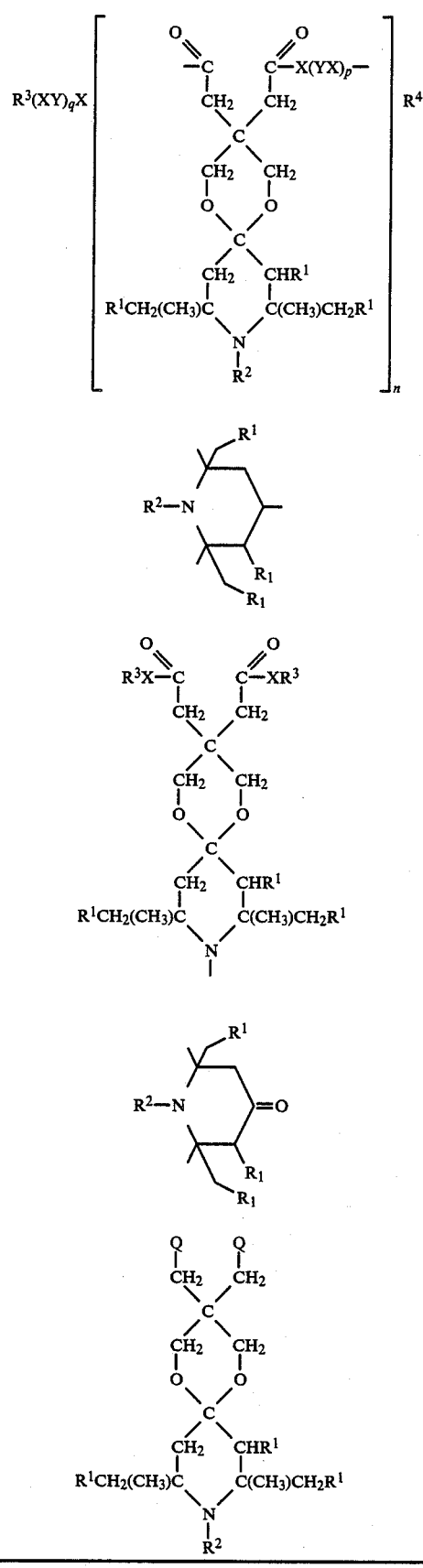

What is claimed is:

1. A compound of the formula I:
wherein n has a value of 1 to 15, when n is 1, p and q is 1 or 0: when n is greater than 1, p is 1 while q may be 1 or 0:

$R^1$ is selected from hydrogen and an alkyl group of 1 to 5 carbon atoms:

$R^2$ is selected from hydrogen, oxyl, hydroxyl, a straight or branched chain methylene-linked alkyl group from 1 to 18 carbon atoms, an alkanoyl group having 2 to 18 carbon atoms, an alkenyl group of 3 to 4 carbon atoms, an alkenoyl group having 3 to 6 carbon atoms, an alkynyl group having 3 to 6 carbon atoms, a cyanomethyl group, a 2,3-epoxy propyl group, an aralkyl group of 7 to 15 carbon atoms, a group $-CH_2CH(OR^5)-R^6$, and a group of the formula $-(CH_2)_mC(O)-Z$ where m is either 1 or 0 and Z is a group selected from $-OR^7$, $-N(R^8)(R^9)$ and $-A-C(O)-R^{10}$ and when m is 0, Z can be a group $-C(O)-OR''$;

$R^3$ and $R^4$ are selected from an llkyl group of 1 to 18 carbon atoms, hydrogen and a group of formula II;

$R^5$ is selected from hydrogen, an aliphatic group of 1 to 18 carbon atoms such as those of $R^2$, an araliphatic group such as benzyl and phenethyl, and an aliphatic acyl group of 2 to 18 carbon atoms such as those of $R^2$;

$R^6$ is selected from hydrogen, an alkyl group of 1 to 16 carbon atoms and penyl;

$R^7$ is selected from an alkyl group of 1 to 18 carbon atoms, a cycloalkyl group of 5 to 12 carbon atoms, allyl, benzyl, phenyl, and a group of formula II wherein $R^1$ and $R^2$ are as described above;

$R^8$ and $R^9$, same or different, are selected from hydrogen, an alkyl group having 1 to 8 carbon atoms, a cycloalkyl group having 5 to 12 carbon atoms such as those of $R^7$, an aryl group having 6 to 10 carbon atoms, and an aralkyl group having 7 to 15 carbon atoms, $R^8$ and $R^9$ may also, together with the nitrogen atom to which they ar attached, form a 5 to 7-membered ring:

A is selected from an alkylene group of.1 to 12 carbon atoms, phenylene and a group $-NH-R^{12}-NH-$ where $R^{12}$ is selected from an alkylene group of 2 to 18 carbon atoms, a cycloalkylene group of 5 to 18 carbon atoms, an aralkylene group having 7 to 18 carbon atoms, an alkylene group having 6 to 18 carbon atoms;

$R^{10}$ is a group of the formula III;

$R^{11}$ is selected from an alkyl group of 1to 18 carbon atoms, phenyl and benzyl;

X is either $-O-$ or $-NR^{13}-$ where $R^{13}$ is selected from hydrogen or an alkyl group of 1 to 8 carbon atoms; and Y is selected from a divalent alkylene group having 2 to 20 carbon atoms, either straight-chained or branched, wherein the alkylene may be interrupted by $-O-$, $-S-$ or $-NR^{13}-$, a cycloalkylene group of 6-12 carbon atoms, a dialkanylcyclohexane, a phenylene group, an aralkylene group having 8 to 19 carbon atoms, and an ethoxy substituted aralkylene group, wherein said formulas are:

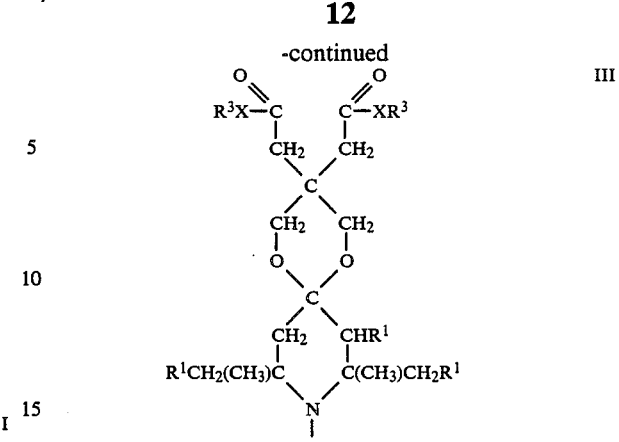

2. A compound of claim 1 wherein $R^1$ is hydrogen and X is —O—.

3. A compound of claim 2 wherein p and q are 0.

4. A compound of claim 3 which is 8,8,10,10-tetramethyl-1,5-dioxa-9-azaspiro[5.5]undecane-3,3-diacetic acid, dimethyl ester.

5. A compound of claim 3 which is 8,8,10, 10-tetramethyl-1,5-dioxa-9-azaspiro[5.5]undecane-3,3-diacetic acid, diester with 2,2,6,6-tetramethyl-piperidin-4-ol.

6. A compound of claim 2 wherein p is 1 and q is 1 or 0.

7. A compound of claim 6 wherein n has a value between 3 and 8.

8. A compound of claim 7 wherein Y is the 2,2-dimethyl-1,3-propylene group and $R^2$ is hydrogen.

9. A synthetic polymer composition stabilized against light induced deterioration comprising an organic polymer normally subjected to deterioration by light, and from 0.01–5% by weight of a compound of the general formula of claim 1.

10. A composition of claim 9 wherein the organic polymer is a polyolefin homopolymer or copolymer.

11. A composition of claim 10 wherein sid organic polymer is a homo or copolymer of polypropylene.

12. A compound of the formula V wherein Q is —CN;

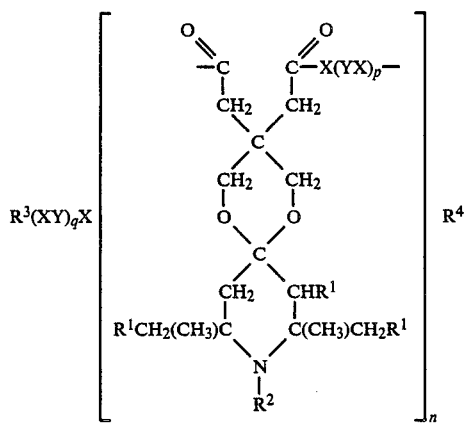

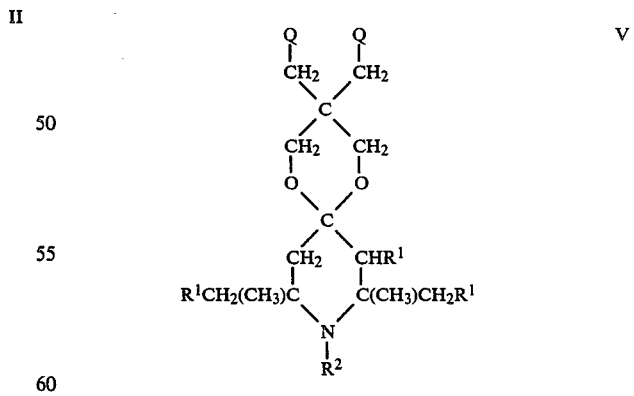

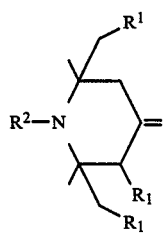

* * * * *

UNITED STATES PATENT AND TRADEMARK OFFICE
CERTIFICATE OF CORRECTION

PATENT NO. : 4,804,699

DATED : February 14, 1989

INVENTOR(S) : Richard V. Nelson and John F. Stephen

It is certified that error appears in the above-identified patent and that said Letters Patent is hereby corrected as shown below:

Formula II, column 9, lines 20-28 and column 11, lines 46-54, should read as follows:

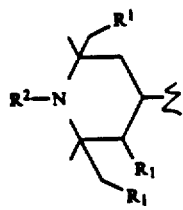

UNITED STATES PATENT AND TRADEMARK OFFICE
CERTIFICATE OF CORRECTION

PATENT NO. : 4,804,699

DATED : February 14, 1989

INVENTOR(S) : Richard V. Nelson and John F. Stephen

It is certified that error appears in the above-identified patent and that said Letters Patent is hereby corrected as shown below:

Formula III, column 9, lines 29-43 and column 12, lines 1-17, should read as follows:

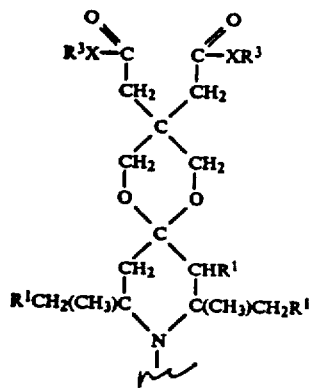

Signed and Sealed this

Twenty-fifth Day of July, 1989

Attest:

DONALD J. QUIGG

Attesting Officer

Commissioner of Patents and Trademarks